(12) United States Patent
Fujisaki et al.

(10) Patent No.: US 8,366,893 B2
(45) Date of Patent: Feb. 5, 2013

(54) PUMPING ELECTRODE OF GAS SENSOR, METHOD OF MANUFACTURING CONDUCTIVE PASTE, AND GAS SENSOR

(75) Inventors: Shinji Fujisaki, Kuwana (JP); Aya Sato, Nagoya (JP); Yukimasa Mori, Nagoya (JP); Sumiko Horisaka, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 207 days.

(21) Appl. No.: 12/732,298

(22) Filed: Mar. 26, 2010

(65) Prior Publication Data

US 2010/0243447 A1    Sep. 30, 2010

(30) Foreign Application Priority Data

Mar. 30, 2009   (JP) .................. 2009-081666

(51) Int. Cl.
*G01N 27/26* (2006.01)
(52) U.S. Cl. ........ 204/424; 204/425; 204/426; 204/427; 204/428; 204/429; 73/23.31; 73/23.32
(58) Field of Classification Search .......... 204/424–429; 205/783.5–785; 73/23.31, 23.32
See application file for complete search history.

(56) References Cited

U.S. PATENT DOCUMENTS 5,902,469 A    5/1999  Kato et al.
5,989,624 A    11/1999 Kida et al.
2003/0121801 A1    7/2003  Inaba et al.
2007/0084723 A1    4/2007  Mizutani et al.
2009/0114539 A1    5/2009  Ziegler et al.

FOREIGN PATENT DOCUMENTS

| DE | 10 2005 049 775 A1 | 4/2007 |
| EP | 0 859 233 A2 | 8/1998 |
| EP | 1 500 931 A2 | 1/2005 |
| JP | 2001-066289 | 3/2001 |
| JP | 2003-09227 A1 | 3/2003 |
| JP | 2006-284223 | 10/2006 |

*Primary Examiner* — Milton I Cano
*Assistant Examiner* — Maris R Kessel
(74) *Attorney, Agent, or Firm* — Burr & Brown

(57) ABSTRACT

A gas sensor including a pump electrode and a method for manufacturing a conductive paste for forming the pump electrode. When the pump electrode constituting an electrochemical pump cell for adjusting an oxygen partial pressure inside a gas sensor to measure a concentration of a gas component in a measurement gas by a current-limiting method is formed of a cermet of a noble metal and an oxide having oxygen ion conductivity, the noble metal contains a first noble metal having a catalytic activity, and a second noble metal having a catalytic activity suppressing ability to suppress the catalytic activity of the first noble metal with respect to an oxide gas except for oxygen, and an abundance ratio of the second noble metal with respect to the first noble metal in a particle surface of the first noble metal existing in the pump electrode is to be 0.01 to 0.3.

5 Claims, 6 Drawing Sheets

F I G . 8
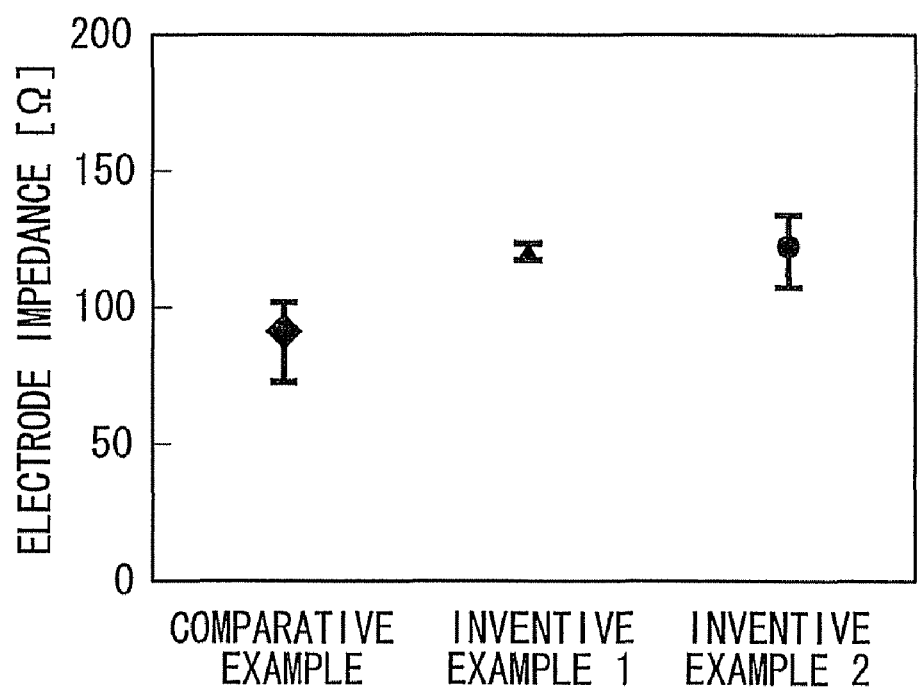

PUMPING ELECTRODE OF GAS SENSOR, METHOD OF MANUFACTURING CONDUCTIVE PASTE, AND GAS SENSOR

BACKGROUND OF THE INVENTION

1. Field of the Invention

The present invention relates to a pump electrode of a gas sensor such as a NOx sensor, and a conductive paste used to form the same.

2. Description of the Related Art

Conventionally, various kinds of measurement devices are used to know a concentration of a desired gas component in a measurement gas. For example, as a device to measure a NOx concentration in a measurement gas such as a combustion gas, a NOx sensor formed of an oxygen ion conducting solid electrolyte such as zirconia ($ZrO_2$) is well known (refer to Japanese Patent Application Laid-Open No. 2006-284223 and U.S. Pat. No. 3,537,983, for example).

In a NOx sensor using current-limiting method as disclosed in the Japanese Patent Application Laid-Open No. 2006-284223 or the U.S. Pat. No. 3,537,983, a NOx concentration in a measurement gas is determined based on the fact that there is a linear relation between a current value of a current (NOx current) flowing when an oxygen ion generated due to reduction or decomposition of NOx in a measurement electrode is pumped by a measurement pump cell serving as an electrochemical pump cell, and the NOx concentration.

Here, in the NOx sensor using the current-limiting method, the introduced measurement gas needs to be supplied to the measurement electrode after the gas is put into a sufficiently low oxygen partial pressure state, in order to ensure measurement accuracy of the NOx concentration. When the NOx sensor is what is called a serial two-chamber structure type disclosed in the Japanese Patent Application Laid-Open No. 2006-284223 or the U.S. Pat. No. 3,537,983, first, the measurement gas is introduced into a first chamber (referred to as an inner space also) and its oxygen concentration is adjusted to be approximately constant by a pumping operation (oxygen is pumped in or out) of a main pump cell serving as an electrochemical pump cell, and then introduced into a second chamber. In the second chamber, the oxygen is pumped out by a pumping operation of an auxiliary pump cell serving as an electrochemical pump cell similarly, so that the measurement gas is put into a sufficiently low oxygen partial pressure state.

Meanwhile, as for the NOx sensor having the above configuration, if NOx is reduced or decomposed at a certain level or more in the oxygen pumping cell such as the main pump cell or the auxiliary pump cell, the accurate NOx concentration cannot be obtained, as a matter of course. Also, when another oxide gas is decomposed, the control of the oxygen concentration in the chamber is substantially disturbed, so that the measurement accuracy deteriorates. Therefore, in general, a main pump electrode constituting the main pump cell in the chamber and an auxiliary pump electrode constituting the auxiliary pump cell in the chamber are formed of a material whose reducing ability with respect to a NOx component in the measurement gas is weakened. For example, a noble metal powder including Pt as a main component and added with Au, or an alloy powder of Pt and Au is preferably used as one example (refer to Japanese Patent Application Laid-Open No. 11-64272 and Japanese Patent Application Laid-Open No. 2001-66289, for example).

In order to improve the measurement accuracy in the current-limiting type NOx sensor to obtain the NOx concentration based on the above-described principle, it is necessary to reduce the reduction or decomposition of NOx and sufficiently lower the oxygen partial pressure (that is, oxygen concentration) of the measurement gas which is supplied to the measurement electrode to the extent not to affect the measurement of NOx. Therefore, it is necessary to configure the oxygen pumping cell such that the oxygen gas is selectively decomposed and pumped.

In addition, in the process of studying to implement the accurate control of the oxygen concentration, the inventor of the present invention has found the fact that there is a variation in oxygen pumping ability of the main pump cell and the auxiliary pump cell in the NOx sensor even when they are the same lots produced under the same production condition, and the fact that the variation in oxygen pumping ability appears as a variation in inter electrode impedance of the main pump electrode and the auxiliary pump electrode, in the NOx sensor produced by the conventional method. Since the variation in lot-to-lot oxygen pump ability prevents a NOx sensor quality from being stabilized, it has to be eliminated.

SUMMARY OF THE INVENTION

The present invention relates to a pump electrode of a gas sensor such as a NOx sensor to measure a concentration of a gas component in a measurement gas by a current-limiting method, and a method for manufacturing an appropriate conductive paste used to form the same.

According to the present invention, a pump electrode provided in an inner space of a gas sensor to measure a concentration of a gas component in a measurement gas by a current-limiting method is characterized in that it constitutes an electrochemical pump cell for adjusting an oxygen partial pressure in the inner space; and is composed of a cermet of a noble metal and an oxide having oxygen ion conductivity, in which the noble metal contains a first noble metal having a catalytic activity, and a second noble metal having a catalytic activity suppressing ability to suppress the catalytic activity of the first noble metal with respect to an oxide gas except for oxygen, and an abundance ratio of the second noble metal with respect to the first noble metal in a particle surface of the first noble metal existing in the pump electrode is 0.01 to 0.3.

Accordingly, it is implemented that the gas sensor has the pump electrode having enhanced selective decomposition ability with respect to oxygen by lowering the catalytic activity with respect the gas except for oxygen, in its inner space.

In addition, according to the present invention, a method for manufacturing a conductive paste used to form the pump electrode includes the following steps: a) preparing a powder of the first noble metal; b) obtaining an ion-containing liquid by dissolving salt or an organic metal complex containing an ion of the second noble metal; and c) mixing the powder of the first noble metal, the ion-containing liquid, a powder of the oxide having the oxygen ion conductivity, and binder.

Accordingly, while the catalytic activity of the pump electrode provided in the inner space can be appropriately lowered, the lot-to-lot variation in abundance ratio of the second noble metal with respect to the first noble metal in the particle surface of the first noble metal existing in the pump electrode, and the lot-to-lot variation in selective decomposition ability with respect to oxygen can be appropriately suppressed. Consequently, the stable-quality gas sensor is implemented.

In addition, according to another aspect, a method for manufacturing a conductive paste used to form the pump electrode includes the following steps: a) preparing a powder of the first noble metal; b) coating the powder of the first noble metal with the second noble metal; and c) mixing the coated powder obtained in the step b), a powder of the oxide having the oxygen ion conductivity, and a binder.

Accordingly, while the catalytic activity of the pump electrode provided in the inner space can be appropriately lowered, the lot-to-lot variation in abundance ratio of the second noble metal with respect to the first noble metal in the particle surface of the first noble metal existing in the pump electrode can be appropriately suppressed. Consequently, the stable-quality gas sensor is implemented.

Therefore, it is an object of the present invention to provide a gas sensor provided with a pump electrode having high selective decomposition ability with respect to an oxygen gas, in its inner space, and to provide a method for manufacturing a conductive paste capable of forming such pump electrode stably.

BRIEF DESCRIPTION OF THE DRAWINGS

FIG. 8 is a view showing a result of measurement of electrode impedance.

DETAILED DESCRIPTION OF THE INVENTION

<First Embodiment>
<Schematic Configuration of Gas Sensor>

First, a description will be made of a schematic configuration of a gas sensor 100.

Figure 1:
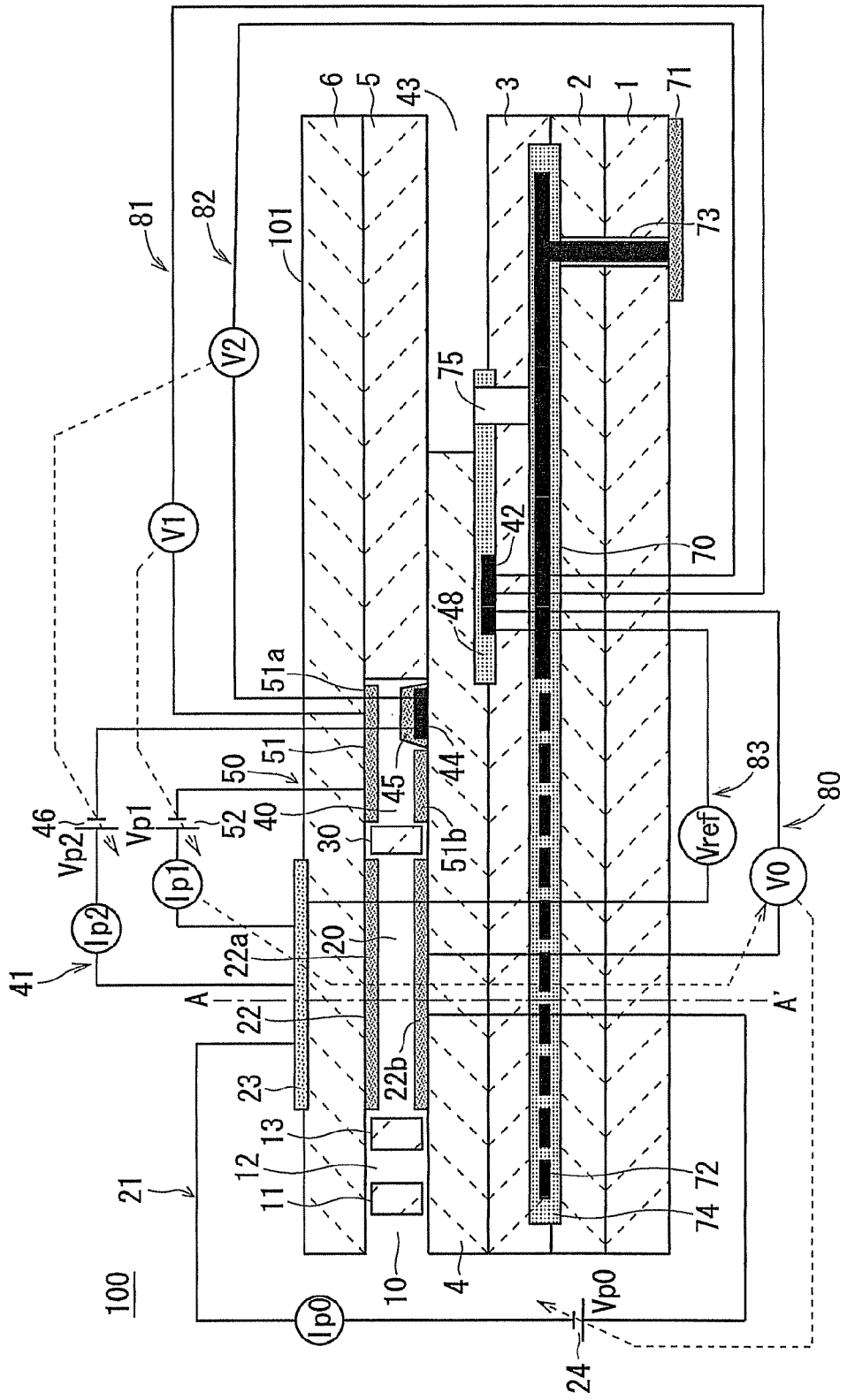
FIG. 1 is a schematic cross-sectional view schematically showing one example of a gas sensor 100.

FIG. 1 is a schematic cross-sectional view schematically showing one example of the configuration of the gas sensor 100. A sensor 101 is an elongated element of a plate-shaped configuration having a structure in which six layers of a first substrate layer 1, a second substrate layer 2, a third substrate layer 3, a first solid electrolyte layer 4, a spacer layer 5, and a second solid electrolyte layer 6 are laminated in this order from the lower side in the drawing, each of the layers being composed of an oxygen ion conducting solid electrolyte layers such as zirconia ($ZrO_2$). In addition, the solid electrolyte configuring those six layers is densely airtight. The sensor element 101 is provided in such a manner that after a predetermined process and printing of a circuit pattern are performed on a ceramic green sheet corresponding to each layer, they are laminated and integrated by baking.

A gas inlet 10, a first diffusion-controlling part 11, a buffer space 12, a second diffusion-controlling part 13, a first inner space 20, a third diffusion-controlling part 30, and a second inner space 40 are adjacently formed so as to be communicated in this order between a lower surface of the second solid electrolyte layer 6 and an upper surface of the first solid electrolyte layer 4, at one end of the sensor element 101.

The gas inlet 10, the buffer space 12, the first inner space 20, and the second inner space 40 are internal spaces provided by hollowing the spacer layer 5 in the sensor element 101, in which their upper parts are defined by the lower surface of the second solid electrolyte layer 6, their lower parts are defined by the upper surface of the first solid electrolyte layer 4, and their side parts are defined by a side surface of the spacer layer 5.

Each of the first diffusion-controlling part 11, the second diffusion-controlling part 13, and the third diffusion-controlling part 30 is provided as two horizontally long (an opening has a longitudinal direction in a direction perpendicular to the drawing) slits. In addition, a portion from the gas inlet 10 to the second inner space 40 is also referred to as a gas distribution part.

In addition, in a position more distant from the end side than the gas distribution part, a reference gas inlet space 43 is provided between an upper surface of the third substrate layer 3 and a lower surface of the spacer layer 5, in which its side part is defined by a side surface of the first solid electrolyte layer 4. For example, the air is introduced to the reference gas inlet space 43 as a reference gas in measuring the NOx concentration.

An air inlet layer 48 is composed of porous alumina, and the reference gas is introduced to the air inlet layer 48 through the reference gas inlet space 43. In addition, the air inlet layer 48 is formed to cover a reference electrode 42.

The reference electrode 42 is formed so as to be sandwiched between the upper surface of the third substrate layer 3 and the first solid electrolyte layer 4, and as described above, the air inlet layer 48 leading to the reference gas inlet space 43 is provided around the reference electrode 42. In addition, as will be described below, an oxygen concentration (oxygen partial pressure) in the first inner space 20 or the second inner space 40 can be measured using the reference electrode 42.

The gas inlet 10 is a portion open to an external space in the gas distribution part, and a measurement gas is introduced from the external space into the sensor element 101 through the gas inlet 10.

The first diffusion-controlling part 11 is a portion to apply a predetermined diffusion resistance to the measurement gas which is brought in from the gas inlet 10.

The buffer space 12 is a space provided to guide the introduced measurement gas from the first diffusion-controlling part 11 to the second diffusion-controlling part 13.

The second diffusion-controlling part 13 is a portion to apply a predetermined diffusion resistance to the measurement gas which is introduced from the buffer space 12 to the first inner space 20.

When the measurement gas is introduced from the outside the sensor element 101 to the first inner space 20, the measurement gas which was abruptly introduced from the gas inlet 10 into the sensor element 101 due to pressure fluctuation of the measurement gas in the outer space (pulsation of exhaust pressure in the case that the measurement gas is an exhaust gas of a car) is not directly introduced into the first inner space 20 but introduced into the first inner space 20 after the concentration fluctuation of the measurement gas has been negated through the first diffusion-controlling part 11, the buffer space 12, and the second diffusion-controlling part 13. Accordingly, the concentration fluctuation of the measurement gas is negligibly small when the gas is introduced to the first internal space.

The first inner space 20 is provided as a space to adjust an oxygen partial pressure in the measurement gas which has been introduced through the second diffusion-controlling part 13. The oxygen partial pressure is adjusted by an operation of a main pump cell 21.

The main pump cell 21 is an electrochemical pump cell including an inner pump electrode 22 having a ceiling electrode part 22a provided on almost all over the lower surface of the second solid electrolyte layer 6 which faces the first inner space 20, an outer pump electrode 23 provided on the upper surface of the second solid electrolyte layer 6 so as to be exposed to the external space and opposed to the ceiling electrode part 22a, and the second solid electrolyte layer 6 sandwiched between the above electrodes.

The inner pump electrode 22 lie astride the upper and lower solid electrolyte layers (second solid electrolyte layer 6 and the first solid electrolyte layer 4) to define the first inner space 20, and the spacer layer 5 to define the side wall thereof. More specifically, the ceiling electrode part 22a is formed on the lower surface of the second solid electrolyte layer 6 to define a ceiling surface of the first inner space 20, a bottom electrode part 22b is formed on the upper surface of the first solid electrolyte layer 4 to define a bottom surface thereof, and a side electrode part (not shown) is formed on a side wall surface (inner surface) of the spacer layer 5 to define each side wall of the first inner space 20, so as to connect the ceiling electrode part 22a to the bottom electrode part 22b, so that a structure having a tunnel configuration at the portion of the side electrode part is provided.

Each of the inner pump electrode 22 and the outer pump electrode 23 is formed as a porous cermet electrode (cermet electrode including Pt containing Au by 1% and zirconia). However, the inner pump electrode 22 which is in contact with the measurement gas is formed of a material whose reducing ability with respect to NOx component in the measurement gas is weakened. The inner pump electrode 22 will be described in detail below.

The main pump cell 21 can pump out the oxygen in the first inner space 20 to the external space, or pump in the oxygen in the external space into the first inner space 20 by means of applying a desired pump voltage Vp0 between the inner pump electrode 22 and the outer pump electrode 23 so as to generate a pump current Ip0 in a positive direction or negative direction between the inner pump electrode 22 and the outer pump electrode 23.

Moreover, in order to detect the oxygen concentration (oxygen partial pressure) in the atmosphere of the first inner space 20, an electrochemical sensor cell, that is, a main-pump controlling oxygen-partial-pressure detection sensor cell 80 includes the inner pump electrode 22, the second solid electrolyte layer 6, the spacer layer 5, the first solid electrolyte layer 4, the third substrate layer 3, and the reference electrode 42.

The oxygen concentration (oxygen partial pressure) in the first inner space 20 can be found by measuring an electromotive force V0 in the main-pump-controlling oxygen-partial-pressure detection sensor cell 80. Furthermore, the pump current Ip0 is controlled by feedback-controlling the Vp0 to keep the electromotive force constant. Thus, the oxygen concentration in the first inner space 20 can be kept at a predetermined value.

The first diffusion-controlling part 30 is a portion to apply a predetermined diffusion resistance to the measurement gas whose oxygen concentration (oxygen partial pressure) has been controlled in the first inner space 20 by the operation of the main pump cell 21, and introduces the measurement gas to the second inner space 40.

The second inner space 40 is provided to perform an operation regarding the measurement of a nitrogen oxide (NOx) concentration in the measurement gas which has been introduced through the third diffusion-controlling part 30. The NOx concentration is mainly measured in the second inner space 40 whose oxygen concentration has been adjusted by an auxiliary pump cell 50, by an operation of a measurement pump cell 41.

After the oxygen concentration (oxygen partial pressure) has been previously adjusted in the first inner space 20, the oxygen partial pressure of the measurement gas which has been introduced through the third diffusion-controlling part is further adjusted by the auxiliary pump cell 50 in the second inner space 40. Therefore, since the oxygen concentration in the second inner space 40 can be kept constant with a high degree of accuracy, the gas sensor 100 can measure the NOx concentration with a high degree of accuracy.

The auxiliary pump cell 50 is an auxiliary electrochemical pump cell including an auxiliary pump electrode 51 having a ceiling electrode part 51a provided on almost a whole lower surface of the second solid electrolyte layer 6 which faces the second inner space 40, the outer pump electrode 23 (not limited to the outer pump electrode 23 but may be an appropriate electrode positioned outside the sensor element 101), and the second solid electrolyte layer 6.

The auxiliary pump electrode 51 is provided in the second inner space 40 so as to have a tunnel structure similar to the inner pump electrode 22 provided in the first inner space 20. That is, the ceiling electrode part 51a is formed on the second solid electrolyte layer 6 defining a ceiling surface of the second inner space 40, a bottom electrode part 51b is formed on the first solid electrolyte layer 4 defining a bottom surface of the second inner space 40, and a side electrode part (not shown) to connect the ceiling electrode part 51a to the bottom electrode part 51b is provided on each wall surface of the spacer layer 5 defining a side wall of the second inner space 40.

In addition, the auxiliary pump electrode 51 is also formed of a material whose reducing ability with respect to the NOx component in the measurement gas is weakened similar to the inner pump electrode 22. The auxiliary pump electrode 51 will be described in detail below together with the inner pump electrode 22.

The auxiliary pump cell 50 can pump out the oxygen in the atmosphere of the second inner space 40 to the external space, or pump in the oxygen in the external space into the second inner space 40 by means of applying a desired pump voltage Vp1 between the auxiliary pump electrode 51 and the outer pump electrode 23.

Moreover, in order to control the oxygen partial pressure in the atmosphere of the second inner space 40, an auxiliary-pump-controlling oxygen-partial-pressure detection sensor cell 81 includes the auxiliary pump electrode 51, the reference electrode 42, the second solid electrolyte layer 6, the spacer layer 5, the first solid electrolyte layer 4, and the third substrate layer 3.

In this regard, the auxiliary pump cell 50 is pumped by a variable power supply 52 whose voltage is controlled based on an electromotive force V1 detected by the auxiliary-pump-controlling oxygen-partial-pressure detection sensor cell 81. Thus, the oxygen partial pressure in the atmosphere of the second inner space 40 can be lowered so as not to substantially affect the measurement of NOx.

In addition, at the same time, its pump current Ip1 is used to control the electromotive force of the main-pump-controlling oxygen-partial-pressure detection sensor cell 80. More specifically, the pump current Ip1 is inputted to the main-pump-controlling oxygen-partial-pressure detection sensor cell 80 as a control signal and then its electromotive force V0 is controlled, so that an inclination of the oxygen partial pressure in the measurement gas which is introduced from the third diffusion-controlling part 30 to the second inner space 40 is controlled to be always kept constant. When used as the NOx sensor, the oxygen concentration in the second inner space 40 is kept at a constant value such as about 0.001 ppm, by the operations of the main pump cell 21 and the auxiliary pump cell 50.

The measuring pump cell 41 measures the NOx concentration in the measurement gas, in the second inner space 40. The measuring pump cell 41 is an electrochemical pump cell including a measurement electrode 44 provided on the upper surface of the first solid electrolyte layer 4 which faces the second inner space 40 so as to be apart from the third diffusion-controlling part 30, the outer pump electrode 23, the second solid electrolyte layer 6, the spacer layer 5, and the first solid electrolyte layer 4.

The measurement electrode 44 is a porous cermet electrode. The measurement electrode 44 also functions as a NOx reducing catalyst to reduce NOx existing in the atmosphere of the second inner space 40. Furthermore, the measurement electrode 44 is covered with a fourth diffusion-controlling part 45.

The fourth diffusion-controlling part 45 is a film made of a porous body mostly including alumina ($Al_2O_3$). The fourth diffusion-controlling part 45 takes a roll in limiting a NOx amount flowing into the measurement electrode 44, and also functions as a protection film of the measurement electrode 44.

The measuring pump cell 41 pumps out the oxygen generated due to decomposition of the nitrogen oxide in the atmosphere around the measurement electrode 44, and can detect its generation amount as a pump current Ip2.

Moreover, in order to detect an oxygen partial pressure around the measurement electrode 44, an electrochemical sensor cell, that is, a measuring-pump-controlling oxygen-partial-pressure detection sensor cell 82 includes the second solid electrolyte layer 6, the spacer layer 5, the first solid electrolyte layer 4, the third substrate layer 3, the measurement electrode 44, and the reference electrode 42. A variable power supply 46 is controlled based on a control voltage V2 detected by the measuring-pump-controlling oxygen-partial-pressure detection sensor cell 82.

The measurement gas which has been introduced in the second inner space 40 reaches the measurement electrode 44 through the fourth diffusion-controlling part 45 under the condition that its oxygen partial pressure is controlled. The nitrogen oxide in the measurement gas around the measurement electrode 44 is reduced and oxygen is generated ($2NO \rightarrow N_2+O_2$). Thus, the generated oxygen is pumped by the measuring pump cell 41, and at this time a voltage Vp2 of the variable power supply is controlled so that the control voltage V2 detected by the measuring-pump-controlling oxygen-partial-pressure detection sensor cell 82 can be kept constant. Since the amount of oxygen generated around the measurement electrode 44 is proportional to the concentration of the nitrogen oxide in the measurement gas, the concentration of the nitrogen oxide in the measurement gas is calculated using the pump current Ip2 in the measuring pump cell 41.

In addition, if oxygen partial pressure detecting means is provided by combining the measurement electrode 42, the first solid electrolyte layer 4, the third substrate layer 3, and the reference electrode 44, as an electrochemical sensor cell, an electromotive force can be detected based on a difference between the oxygen amount generated due to the reduction of the NOx component in the atmosphere around the measurement electrode 44 and an oxygen amount in the reference air, and as a result, the concentration of the NOx component in the measurement gas can be found.

What is more, an electrochemical sensor cell 83 is constituted of the second solid electrolyte layer 6, the spacer layer 5, the first solid electrolyte layer 4, the third substrate layer 3, the outer pump electrode 23, and the reference electrode 42, and the oxygen partial pressure in the measurement gas outside the sensor can be detected by an electromotive force Vref obtained by this sensor cell 83.

In the gas sensor 100 having the above configuration, the measurement gas whose oxygen partial pressure is always kept at a constant low value (which does not affect the measurement of NOx substantially) by the operations of the main pump cell 21 and the auxiliary pump cell 50 is applied to the measuring pump cell 41. Therefore, the NOx concentration in the measurement gas can be known, based on the pump current Ip2 which flows on the basis that the oxygen generated by the reduction of NOx is pumped out by the measuring pump cell 41, in approximately proportion to the NOx concentration in the measurement gas.

Furthermore, in order to enhance oxygen ion conductivity of the solid electrolyte, the sensor element 101 has a heater part 70 taking a role of temperature regulation to heat the sensor element 101 and keep its temperature. The heater part 70 includes a heater electrode 71, a heater 72, a through hole 73, a heater insulation layer 74, and a pressure diffusion hole 75.

The heater electrode 71 is an electrode formed to be in contact with the lower surface of the first substrate layer 1. When the heater electrode 71 is connected to an external power supply, a power can be supplied to the heater part 70 from the outside.

The heater 72 is an electric resistor formed to be sandwiched between the second substrate layer 2 and the third substrate layer 3 vertically. The heater 72 is connected to the heater electrode 71 through the through hole 73, and generates heat when a power is supplied from the outside through the heater electrode 71, and heats the solid electrolyte forming the sensor element 101 and keeps its temperature.

Then, the heater 72 is buried all over the region from the first inner space 20 to the second inner space 40, and can regulate the temperature in the whole sensor element 101 so that the solid electrolyte can be activated.

The heater insulation layer 74 is formed of an insulator such as alumina, on upper and lower surfaces of the heater 72. The heater insulation layer 74 is formed with a view to obtaining electric insulation between the second substrate layer 2 and the heater 72, and electric insulation between the third substrate layer 3 and the heater 72.

The pressure diffusion hole 75 is a portion configured to penetrate the third substrate layer 3 and communicate with the reference gas inlet space 43, and formed with a view to lessening an inner pressure from rising with the temperature rise in the heater insulation layer 74.

<Process for Manufacturing Sensor Element>

Then, a description will be made of a process for manufacturing the sensor element 101 having the above structure. According to this embodiment, the laminated body composed of the green sheets containing an oxygen ion conducting solid electrolyte such as zirconia as a ceramic component is formed, and the sensor element 101 is made by cutting and baking the laminated body.

Hereinafter, a description will be made of a case where the sensor element 101 including the six layers as shown in FIG. 1 is produced as one example. In this case, the six green sheets are prepared so as to correspond to the first substrate layer 1, the second substrate layer 2, the third substrate layer 3, the first solid electrolyte layer 4, the spacer layer 5, the second solid electrolyte layer 6.

Figure 2:
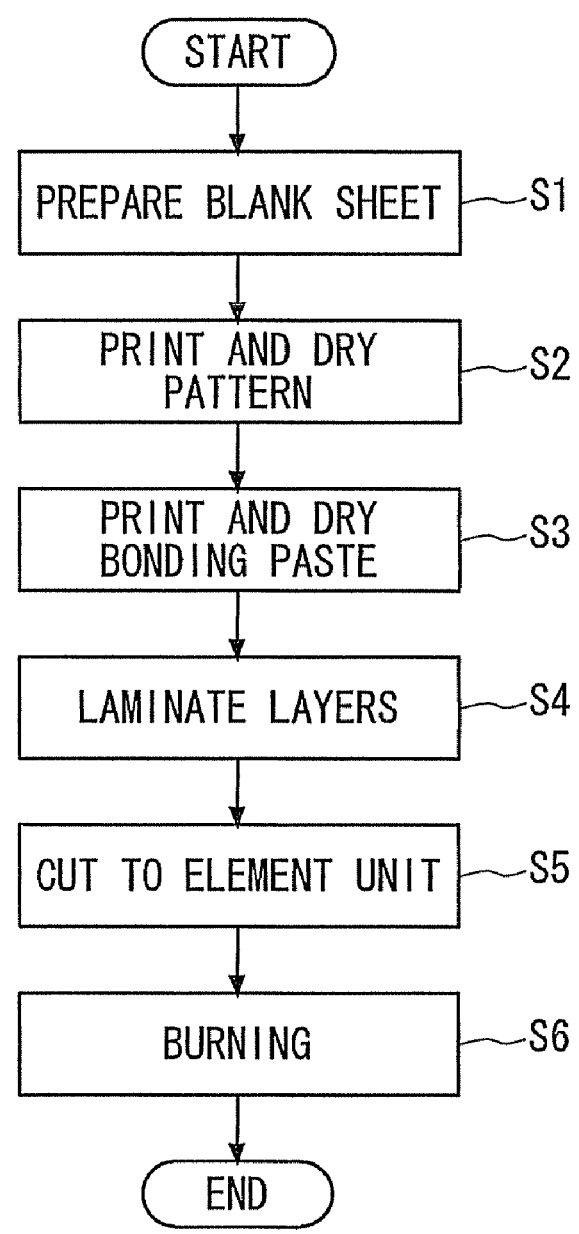
FIG. 2 is a view showing a flow of processes when a sensor element 101 is formed.

FIG. 2 is a view showing a flow of the processes when the sensor element 101 is fabricated. When the sensor element 101 is fabricated, first, a blank sheet (not shown) that is a green sheet on which a pattern is not formed is prepared (step S1). When the sensor element 101 is composed of the six layers, the six blank sheets are prepared for the respective layers. The blank sheet is provided with a plurality of sheet holes to be used for positioning at the time of printing and laminating. The sheet hole is previously formed at the stage of the blank sheet prior to pattern formation, through a punching process by a punching device. In addition, in the case of the green sheet whose corresponding layer provides an internal space, a penetrating part corresponding to the internal space is formed by the same punching process. In addition, a thickness of the blank sheet corresponding to each layer of the sensor element 101 is not necessarily the same.

After the preparation of the blank sheets corresponding to the respective layers, a printing and drying processes to form an individual pattern on each blank sheet are performed (step S2). More specifically, electrode patterns of the inner pump electrode 22, the outer pump electrode 23, the reference electrode 42, the measurement electrode 44, and the auxiliary pump electrode 51, and the fourth diffusion-controlling part 45, and the air inlet layer 48, and an internal wiring which is not shown are formed. In addition, a cut mark is printed in the first substrate layer 1 to be used as a reference of a cut position when the laminated layer body is cut in a post processing step.

Each pattern is printed by applying a pattern forming paste prepared based on the characteristics required for the object to be formed, to the blank sheet by a well-known screen printing technique. The drying process after the printing process may be performed by well-known drying means.

In this embodiment, a way of preparing the conductive paste used to form the inner pump electrode 22 and the auxiliary pump electrode 51 which are pump electrodes provided in the first inner space 20 and the second inner space 40 is characteristic. Its detailed description will be made below.

After the pattern printing, printing and drying processes are performed for a bonding paste to laminate and bond the green sheets corresponding to the respective layers (step S3). The printing of the bonding paste can be performed by a well-known screen printing technique, and the drying process after the printing can be performed by well-known means.

Then, a crimping process is performed by laminating the green sheets each applied with a bonding agent in the predetermined order, and pressing them under predetermined temperature and pressure to form one laminated body (step S4). More specifically, the green sheets to be laminated are laminated and held in a predetermined laminating jig which is not shown while they are positioned by the sheet holes, and the entire laminating jig is heated and pressed by a laminating machine such as a well-known hydraulic press machine. While the pressure, temperature, and time in the heating and pressing operations depend on the used laminating machine, they may be determined under appropriate conditions so as to implement preferable lamination.

After the laminated body is obtained as described above, the laminated body is cut into a plurality of parts to provide a unit (referred to as an element body) of the individual sensor element 101 (step S5). The cut element body is burned under a predetermined condition, whereby the sensor element 101 having the above-described outer shape is produced (step S6). The sensor element 101 obtained as described above is put in a predetermined housing, and assembled in a main body (not shown) of the gas sensor 100.

<Detailed Configuration of Inner-Space Pump Electrode>

Next, a description will be made of detailed configurations of the inner pump electrode 22 and the auxiliary pump electrode 51 which are characteristic in this embodiment. In the following description, the inner pump electrode 22 and the auxiliary pump electrode 51 are collectively referred to as an inner-space pump electrode.

As described above, according to this embodiment, the inner-space pump electrode is formed of the material whose reducing ability with respect to the NO component in the measurement gas is weakened. This is implemented by adding gold (Au) as a conductive component (noble metal component) of the inner-space pump as well as platinum (Pt) which is a main component. Note that a volume ratio of the noble metal component and zirconia is preferably 5:5 to 8:2.

The addition of Au allows for lowering a catalytic activity with respect to oxide gaseous species except for oxygen in the inner-space pump electrode (suppressing decomposition in the electrode), and enhancing selective decomposition ability with respect to oxygen in the inner-space pump electrode. Here, an amount of the catalytic activity with respect to the oxide gaseous species except for oxygen can be determined by an exposed amount of Pt in the electrode, so that it means that the smaller the exposed amount of Pt is, the smaller the catalytic activity is. In addition, the exposed amount of Pt can be found by a CO pulse adsorption method. The "catalytic activity" means the catalytic activity with respect to the oxide gaseous species except for oxygen in the following description unless otherwise noted.

More specifically, in this embodiment, it is preferable that when the inner-space pump electrode is formed, Au is added in such a manner that an abundance ratio of Au (Au abundance ratio) in a surface of a Pt particle existing in the inner-space pump electrode becomes 0.01 to 0.3. In this case, the catalytic activity in the inner-space pump electrode can be appropriately lowered and the selective decomposition ability with respect to oxygen is enhanced.

In addition, in this embodiment, the Au abundance ratio means an area ratio of a part covered with Au with respect to a part not covered with Au where the Pt particle itself is exposed, in the Pt particle surface in the inner-space pump electrode. In this embodiment, the Au abundance ratio is calculated by a relative sensitivity coefficient method, based on peak intensity of detection peaks of Au and Pt obtained by XPS (X-ray photoelectron spectroscopy) method.

The Au abundance ratio is set to 0.01 or more to preferably obtain an effect of lowering the catalytic activity and preferably ensure a linear relation (linearity) between the NO concentration and the pump current Ip2. In this embodiment, whether the linear relation is good or not is evaluated by an index such as a linearity ratio.

Figure 3:
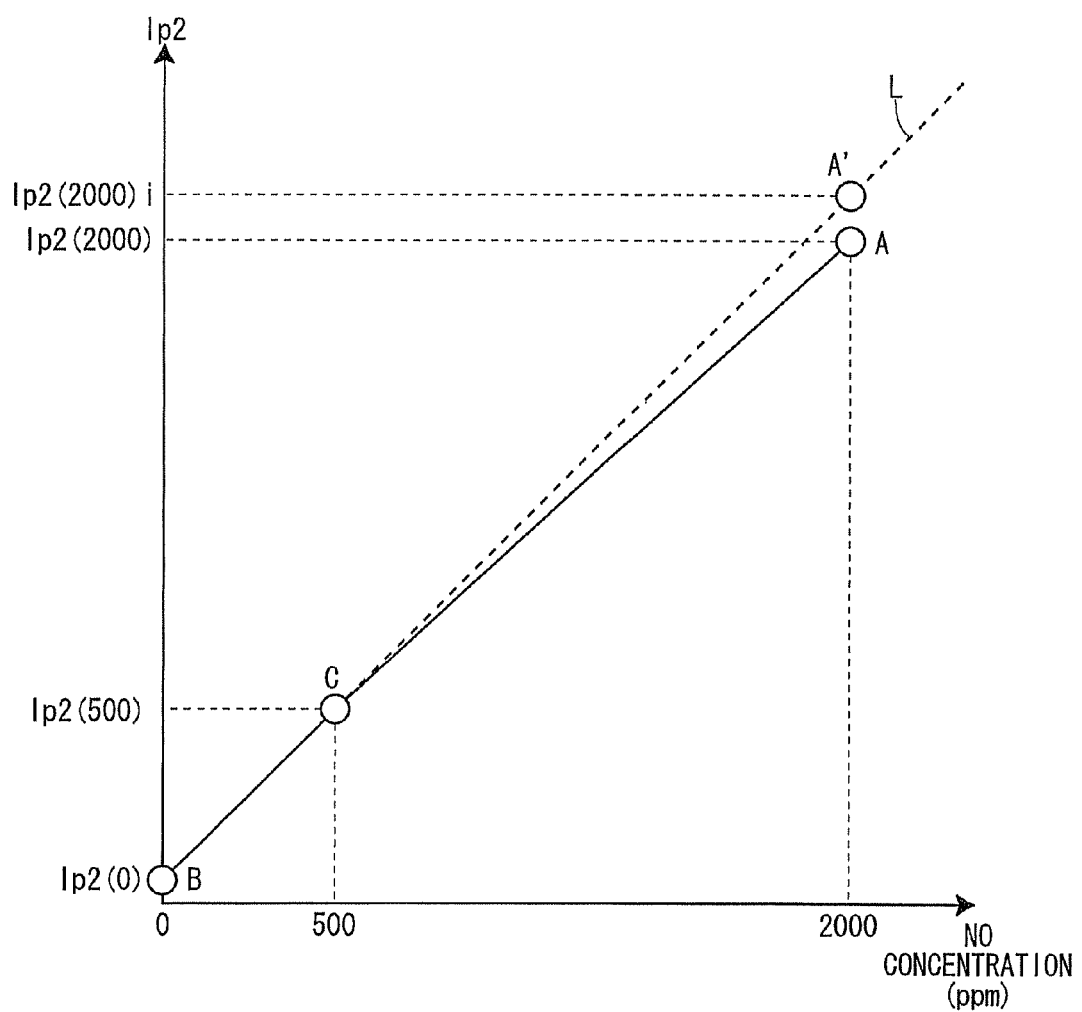
FIG. 3 is a view to explain a linearity ratio.

FIG. 3 is a view to explain the linearity ratio. If the gas sensor 100 has ideal characteristics, a perfect linear relation can be established between the NO concentration and the pump current Ip2, but in the actual gas sensor 100, a shift from this linear relation arises as the NO concentration increases. Thus, the linearity ratio is used as an index showing how much it is close to the perfect linear relation.

More specifically, the linearity ratio is calculated by the following formula.

$$\text{Linearity ratio}(\%) = \frac{Ip2(2000) - Ip2(0)}{Ip2(2000)i - Ip2(0)} \times 100$$

$$= \frac{Ip2(2000) - Ip2(0)}{\{Ip2(500) - Ip2(0)\} \times (2000/500)} \times 100$$

This formula shows how much the pump current value Ip2 (2000) when the NO concentration is 2000 ppm shown by a point A in FIG. 3 is close to an ideal pump current value Ip2

(2000)i shown by a point A' on a broken line L, which is an extended line of a line segment provided by connecting a pump current value Ip2 (0) when the NO concentration is 0 ppm shown by a point B and a pump current value Ip2 (500) when the NO concentration is 500 ppm shown by a point C.

It has been confirmed by the inventor of the present invention that when the linearity ratio obtained by the above formula is 95% or more, the linear relation between the NO concentration and the pump current Ip2 can be substantially established, and sufficient measurement accuracy can be practically obtained.

Figure 4:
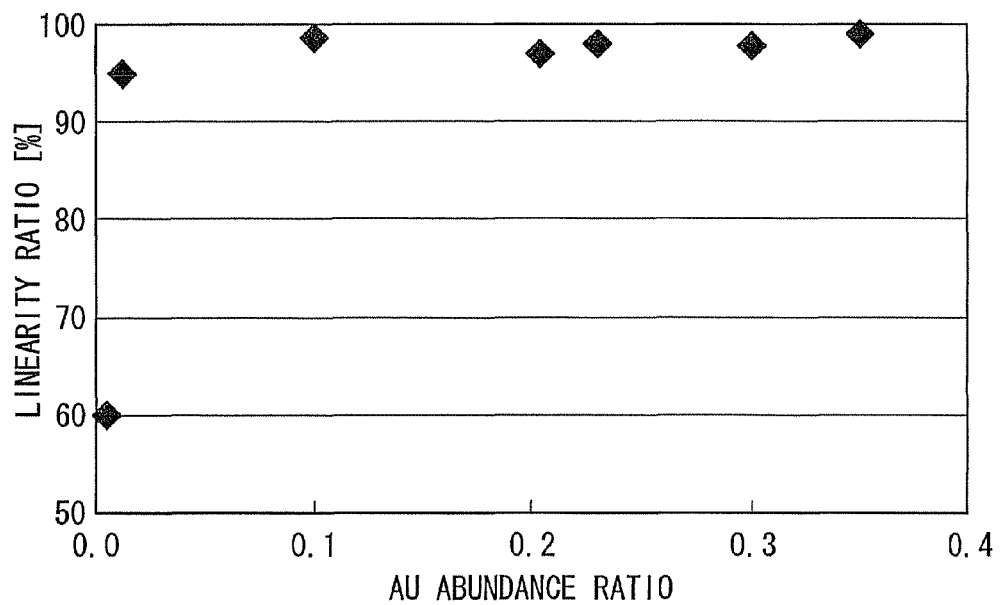
FIG. 4 is a view in which the linearity ratio is plotted on an Au abundance ratio.

FIG. 4 is a view in which the linearity ratio obtained by the above formula is plotted on the Au abundance ratio with respect to various gas sensors having different Au abundance ratios. It is confirmed from FIG. 4 that when the Au abundance ratio is 0.01 or more, the linearity ratio is 95% or more, but when the Au abundance ration is less than 0.01, the linearity ratio abruptly decreases. This result shows that the Au abundance ratio is preferably 0.01 or more.

Meanwhile, the Au abundance ratio is set to 0.3 or less to prevent an interelectrode impedance from increasing in each pump cell. As the interelectrode impedance increases, a value of the voltage to be applied to pump cell to generate a current at a certain level or more increases, but in the case of the current-limiting type gas sensor such as the gas sensor 100 according to this embodiment, excessive voltage application to the pump cell causes decomposition of a material which does not need to be decomposed originally other than oxygen, so that the selective decomposition ability with respect to oxygen becomes unstable, which is not preferable.

Figure 5:
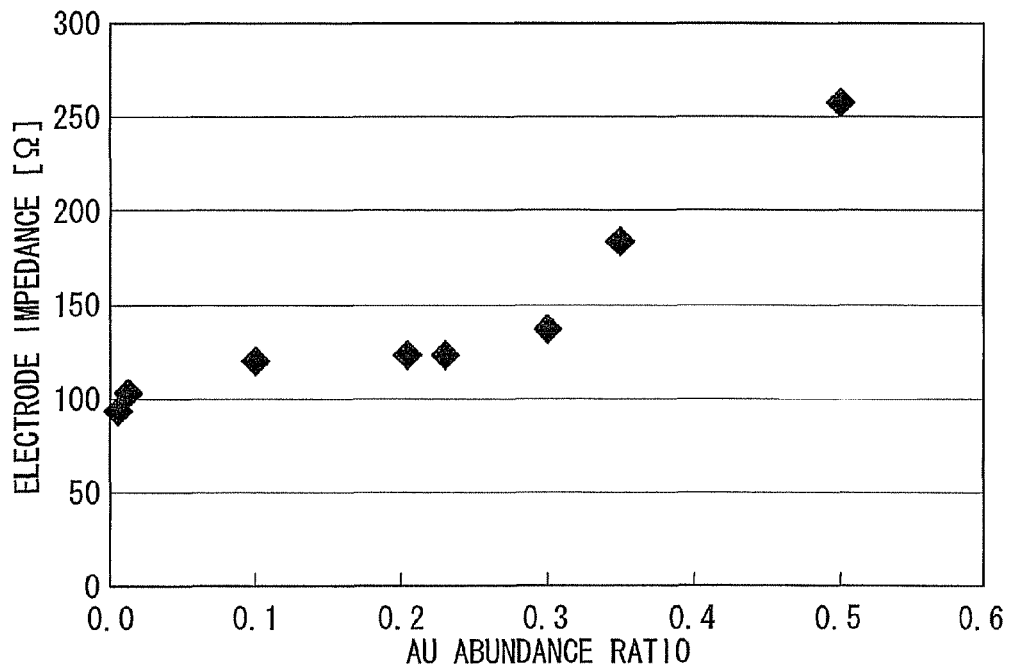
FIG. 5 is a view in which an interelectrode impedance between an outer pump electrode 23 and an inner pump electrode 22 is plotted on the Au abundance ratio.

FIG. 5 is a view in which an interelectrode impedance between the outer pump electrode 23 and the inner pump electrode 22 is plotted on the Au abundance ratio for various gas sensors having respective different Au abundance ratios. It is confirmed from FIG. 5 that when the Au abundance ratio is 0.3 or less, the interelectrode impedance is kept almost constant, but when the Au abundance ratio is more than 0.3, the interelectrode impedance abruptly increases. This result shows that the Au abundance ratio is preferably 0.3 or less.

More preferably, the Au abundance ratio is 0.1 to 0.25 and further preferably, the Au abundance ratio is 0.2 to 0.25. In this case, the exposed amount of Pt in the inner-space pump electrode is reduced to 4/5 to 3/4 of that when the Au abundance ratio is 0.01 or less. Consequently, the effect of reducing the catalytic activity can be sufficiently obtained.

<Conductive Paste for Inner-Space Pump Electrode>

Next, a description will be made of the conductive paste used to form the inner-space pump electrode. Conventionally, the conductive paste for the inner-space pump electrode was made by mixing an alloy powder of Pt and Au, a zirconia powder, and a binder. Alternatively, an additive amount of Au was adjusted as prescribed by mixing a Pt powder, and the alloy powder of Pt and Au in some cases. That is, in either case, a starting raw material of Au in the conductive paste is the alloy powder with Pt. The manufacturing of the conductive paste in the above example is referred to as alloyed-Au powder mixing. However, as for the inner-space pump electrode formed with the conductive paste obtained from the above alloyed-Au powder mixing, the Au abundance ratio in the Pt particle surface of the electrode can not exceed 0.01. That is, even when the conductive paste prepared by the well-known conventional way is used, it is difficult to implement the Au abundance ratio such as 0.01 to 0.3 in the inner-space pump electrode.

According to this embodiment, instead of mixing Au as the alloy powder, a liquid containing an Au ion is used as a starting raw material of Au and the liquid containing the Au ion is mixed with the Pt powder, the zirconia powder, and a binder, whereby the conductive paste for the inner-space pump electrode is manufactured. Note that the binder may appropriately be selected as long as it disperses other materials to extent that a printing is executable and it is eliminated by burning. The manufacturing of the conductive paste in this way is referred to as Au liquid mixing. Here, the liquid containing the Au ion is provided by dissolving salt or an organic metal complex containing the Au ion in a solvent. As the salt containing the Au ion, tetrachloroauric (III) acid (HAuCl4), sodium chloroaurate (III) (NaAuCl$_4$), or potassium dicyanoaurate (I) (KAu (CN)$_2$) may be used. As the organic metal complex containing the Au ion, gold (III) diethylenediamine trichloride ([Au(en)$_2$] Cl$_3$), gold (III) dichloro (1, 10-phenanthroline) chloride ([Au(phen) Cl$_2$] Cl), dimethyl (trifluoroacetylacetonate) gold, or dimethyl (hexafluoroacetylacetonate) gold may be used. Tetrachloroauric (III) acid or gold (III) diethylenediamine chloride ([Au(en)$_2$] Cl$_3$) is preferably used from the viewpoint that an impurity such as Na or K does not remain in the electrode, it is easy to handle, or it is likely to dissolve in the solvent. As the solvent, acetone, acetonitrile, or formamide may be used as well as alcohol such as methanol, ethanol, or propanol. Then, mixing is performed by well-known means such as instillation. Consequently, while Au exists in ionic (or complex ionic) state in the obtained conductive paste for the inner-space pump electrode, Au exists mainly in a state of elementary substance or alloy with Pt in the inner-space pump electrode in the sensor element obtained through the above-described manufacturing process.

With the conductive paste for the inner-space pump electrode produced using the Au liquid mixing, the inner-space pump electrode in which the Au abundance ratio is 0.01 to 0.3 in the surface of the Pt particle can be formed, this Au abundance ratio being difficult to implement in the case where the conventional conductive paste manufactured by the alloyed-Au powder mixing is used. In addition, a lot-to-lot variation in Au abundance ratio can be suppressed to about 10% or less of an average value.

Furthermore, in this case, the Pt exposed amount in the formed inner-space pump electrode can be suppressed to 1/5 or less of that provided when the conductive paste manufactured by the alloyed-Au powder mixing is used. In addition, the former lot-to-lot variation can be reduced to about 1/3 of the latter lot-to-lot variation. Consequently, it is found that to form the inner-space pump electrode with the conductive paste for the inner-space pump electrode produced using the Au liquid mixing is an effective way to lower the catalytic activity in the inner-space pump electrode.

In addition, in this case, the lot-to-lot variation in interelectrode impedance is reduced to about 1/5 of that provided when the paste manufactured by the alloyed-Au powder mixing is used. As a result, a lot-to-lot variation in oxygen pumping ability can be appropriately suppressed.

In general, the amount of the conductive paste used for forming one inner-space pump electrode is sufficiently smaller than the amount of the conductive paste manufactured at one time. In this respect, the fact that the lot-to-lot variation in Au abundance ratio is small means that Au atoms exist in more highly dispersed state in the conductive paste for the inner-space pump electrode manufactured by the Au liquid mixing according to this embodiment, as compared with the conductive paste manufactured by the conventional alloyed-Au powder mixing. As a result, it is found that the method using the Au liquid mixing is a preferable way to produce the conductive paste in which the Au atoms are highly dispersed, and therefore to suppress the interelectrode impedance variation in the pump cell.

Moreover, the fact that the variation in Au abundance ratio is small means that a correlation is high between a weight ratio of Au in the all noble metal elements in the conductive paste for the inner-space pump electrode, and the Au abundance ratio in the surface of the Pt particle in the inner-space pump electrode. Besides, the fact that the variation in interelectrode impedance is small means that a correlation is high between the weight ratio and the interelectrode impedance. In this case, when a composition of the raw material mixture at the time of manufacturing the conductive paste is specified, a composition in the surface of the electrode particle in the pump electrode and therefore the interelectrode impedance are determined based on the specified composition. This means that the composition of the inner-space pump electrode can be controlled with higher accuracy by employing the Au liquid mixing in manufacturing conductive paste for the inner-space pump electrode, and that, as a result, the pumping functions of the main pump electrode and the auxiliary pump electrode can be controlled with a high degree of accuracy.

As described above, according to this embodiment, by setting the abundance ratio in the surface of the Pt particle in the inner-space pump electrodes (inner pump electrode and auxiliary pump electrode) of the sensor element to 0.01 to 0.3, the gas sensor is implemented such that the linear relation between the NO concentration and the pump current Ip2 is kept, and the interelectrode impedances of the main pump cell and the auxiliary pump cell can be suppressed, and the catalytic activity of the inner-space pump electrode is lowered and the selective decomposition ability of oxygen is enhanced.

In addition, the formation of the inner-space pump electrode is implemented using the conductive paste including Au ion-containing liquid. Furthermore, with the use of the conductive paste including the Au ion-containing liquid, the lot-to-lot variation in Au abundance ratio in the surface of the Pt particle in the inner-space pump electrode, and the lot-to-lot variation in oxygen pumping ability are appropriately suppressed. That is, the high correlation can be obtained between the weight ratio of Au in the all noble metal elements in the conductive paste, and the Au abundance ratio in the surface of the Pt particle in the inner-space pump electrode, and between the weight ratio and the electrode impedance. Therefore, with the use of the conductive paste including the Au ion-containing liquid, the composition control and design of the inner-space pump electrode of the gas sensor are more accurately performed. As a result, the quality of the gas sensor can be stabilized.

<Second Embodiment>

While the inner-space pump electrode is formed with the conductive paste manufactured by the Au liquid mixing in the first embodiment, a description will be made of another way of producing a conductive paste for the inner-space pump electrode in this embodiment.

According to this embodiment, as a starting raw material to manufacture a conductive paste for the inner-space pump electrode, a coated powder in which the Pt powder is coated with Au is used. That is, the conductive paste for the inner-space pump electrode is manufactured by mixing the coated powder, the zirconia powder, and a binder. Here, as the coated powder, the one provided by coating the particle surface of the Pt powder with a film of Au may be used or the one provided by bonding an Au particle to the Pt powder particle may be used.

When the conductive paste manufactured by the above coated powder is used also, similar to the first embodiment, the inner-space pump electrode can be formed such that a Au abundance ratio in the Pt particle surface is 0.01 to 0.3, and a Pt exposed amount is reduced to the same level as that of the first embodiment.

Consequently, according to this embodiment also, similar to the first embodiment, by setting the Au abundance ratio in the Pt particle surface of the inner-space pump electrodes (inner pump electrode and auxiliary pump electrode) of the sensor element to 0.01 to 0.3, the gas sensor is implemented such that the linear relation between the NO concentration and the pump current Ip2 is established, and the interelectrode impedances of the main pump cell and the auxiliary pump cell can be suppressed, and the catalytic activity in the inner-space pump electrode is lowered and the selective decomposition ability of oxygen is enhanced.

In addition, in the inner-space pump electrode formed using the conductive paste according to this embodiment also, a lot-to-lot variation in Au abundance ratio in the surface of the Pt particle can be appropriately suppressed. That is, a high correlation can be obtained between a weight ratio of Au in the conductive paste, and the Au abundance ratio in the surface of the Pt particle in the inner-space pump electrode, similar to the first embodiment. Therefore, with the use of the conductive paste according to this embodiment, a composition control and design of the inner-space pump electrode of the gas sensor are more accurately performed. As a result, the quality of the gas sensor can be stabilized.

<Variation>

It is effective for an oxygen sensor of a current-limiting method to use the conductive paste including the Au ion-containing liquid for forming the inner-space pump electrode. In the case of the oxygen sensor also, if an oxygen ion generated by decomposing an oxide gas (NO, $CO_2$, or $H_2O$) except for oxygen flows as an oxygen pump current, measurement accuracy is lowered. That is, in the case of the oxygen sensor also, an oxygen pumping cell is required to be configured to selectively pump an oxygen gas only. In the oxygen sensor also, similar to the above embodiment, by forming the inner-space pump electrode using the conductive paste including Au ion-containing liquid, catalytic activity of the inner-space pump electrode can be lowered, and selective decomposition ability with respect to an oxygen gas can be enhanced.

EXAMPLES

As an inventive example 1 of the sensor element 101 according to the above-described embodiment, a plurality of sensor elements were made with use of the conductive paste manufactured using gold (III) diethylenediamine chloride ($[Au(en)_2] Cl_3$) as the Au ion-containing liquid, for forming the inner-space pump electrodes. In addition, as an inventive example 2, a plurality of sensor elements were made with use of the conductive paste manufactured using Au coated powder provided by coating the particle surface of the Pt powder with the film of Au for forming the inner-space pump electrodes. In each of the inventive examples, the conductive paste for the inner-space pump electrode was manufactured so that the weight ratio of Au in the all noble metal elements might be 0.9 wt %. The volume ratio between the noble metal component and zirconia as the ceramic component was set to 6:4.

Additionally, as a comparison example, a plurality of sensor elements were also made with use of a conductive paste containing Au by the alloy powder mixing for forming inner-space pump electrodes. The production condition and configuration were all the same as those in the first inventive example 1 except that a weight ratio of Au in the all noble metal elements in the conductive paste for the inner-space pump electrode was set to 0.7 wt %.

Catalytic activity evaluation, Au abundance ratio evaluation, and electrode impedance measurement were made with respect to the obtained inner pump electrodes of the sensor elements.

(Catalytic Activity Evaluation by Measuring Pt Exposed Amount)

An exposed amount of Pt surface in the inner pump electrode was evaluated by CO pulse adsorption method. Since it is known that an Au atom hardly adsorbs the CO molecule at room temperature while a Pt atom of the particle surface absorbs one CO molecule, the Pt exposed amount in the inner pump electrode can be measured by measuring a CO absorption amount. That is, the more the CO adsorption amount, the more the Pt atoms are exposed to the surface. For comparison, a pure Pt powder was also measured. The number of lots for measurement was six for each. In addition, prior to the measurement, preheating was performed to remove a previously adsorbing gas and impurity.

Figure 6:
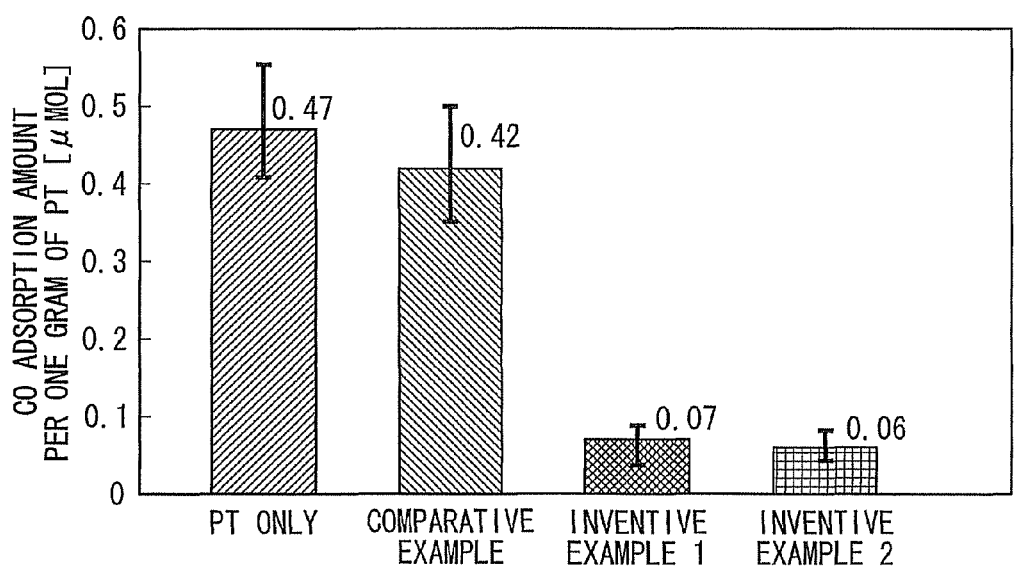
FIG. 6 is a view showing a result of measurement of a Pt exposed amount.

The measurement condition is as follows.
Sample amount: 0.5 g;
Adsorption gas: CO 50%/He balance;
Pulse applying amount: 10 μl/1 pulse FIG. 6 is a view showing a result of measuring the Pt exposed amount. In FIG. 6, a bar chart shows an average value, and an error bar shows a variation (range).

As shown in FIG. 6, the CO adsorption amount corresponding to the Pt exposed amount is considerably small in each of the inventive example 1 and the inventive example 2 as compared with the case of the Pt powder. Meanwhile, the CO adsorption amount is a little smaller in the comparison example than the case of the Pt powder. As a result, it is confirmed that the ways of adding Au in the inventive example 1 and the inventive example 2 are extremely effective to reduce the Pt exposed amount, that is, to reduce the catalytic activity as compared with the alloyed-Au powder mixing according to the comparison example. Furthermore, the fact that the lot-to-lot variation in each of the inventive example 1 and the inventive example 2 is about 1/3 of that of the comparison example means that the catalytic activity can be more stabilized in the inventive example than that of the comparison example.

(Au Abundance Ratio Evaluation)

The Au abundance ratio in the surface of the Pt particle in the inner pump electrode was evaluated by the XPS (X-ray photoelectron spectroscopy) method. The Au abundance ratio was calculated based on the peak intensity of the detection peaks of Au and Pt using a relative sensitivity coefficient method. The number of lots for measurement was six in the inventive examples and eight in the comparison example.

The measurement condition is as follows.
Measurement device: ESCA-5700ci produced by Physical Electronics Inc.;
X-ray source: MgKα (1254.6 eV);
Output: 400 W;
Spectrograph: Pass Energy 23.5 eV;
Detection peak: Au 4 f, Pt 4 f;
Angle between X-ray and sample: 45°;
Angle between X-ray and spectrograph: 54.7°
Calculation software: PHI MultiPak 6.2

Figure 7:
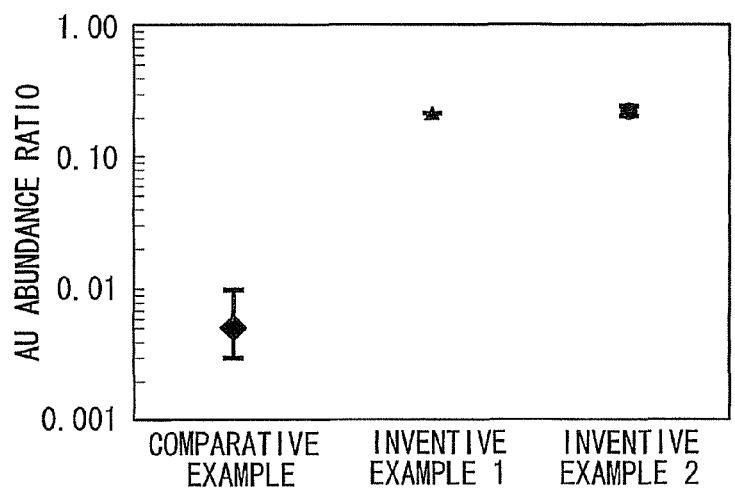
FIG. 7 is a view showing an Au abundance ratio obtained by XPS measurement.

FIG. 7 is a view showing the obtained Au abundance ratio. In FIG. 7, a rhombic mark, a triangle mark, and a circle mark show average values and an error bar shows a variation (range).

As shown in FIG. 7, while the Au abundance ratio in the surface of the Pt particle in the inner pump electrode is within a range of 0.2 to 0.25 in each of the inventive example 1 and the inventive example 2, the Au abundance ratio thereof is 0.01 or less in the comparison example. Taking the result of the measurement of the Pt exposed amount shown in FIG. 6 into consideration, it is said that the catalytic activity is reduced in each of the inventive example 1 and the inventive example 2 when the Au abundance ratio in the surface of the Pt particle in the inner pump electrode is enhanced.

Furthermore, while the Au abundance ratio varies about twice the average value among the lots in the comparison example, the lot-to-lot variation of the Au abundance ratio is reduced to about 10% or less of the average value in each of the inventive example 1 and the inventive example 2. This means that the way of adding Au in each of the inventive example 1 and the inventive example 2 is a highly effective to uniformly disperse Au in the surface of the Pt particle in the inner pump electrode as compared with the way of adding Au by the alloy powder mixing in the comparison example.

(Measurement of Electrode Impedance)

The impedance between the outer pump electrode and the inner pump electrode was measured. More specifically, a measurement gas whose oxygen concentration was known as 18% was introduced into the sensor element 101 at a usual driving temperature of the sensor element 101, and a regression line between a voltage applied between both pump electrodes and a current value flowing at that time was obtained, and an inverse number of its inclination was specified as an impedance value. The number of lots for measurement was six.

FIG. 8 is a view showing the result of measurement of the electrode impedance. A rectangular mark and rhombic mark show average values, and error bar shows a variation (range).

As shown in FIG. 8, although the average value of the impedance value is a little greater in the inventive example 1 than that of the comparison example, the lot-to-lot variation in impedance value is reduced to about 1/5 of the comparison example. This result means that the pumping ability with respect to oxygen in the inner-space pump electrode can be stabilized by adding Au using the Au liquid mixing.

What is claimed is:
1. A pump electrode provided in an inner space of a gas sensor that measures a concentration of a gas component in a measurement gas by a current-limiting method, the gas sensor including an electrochemical pump cell for adjusting an oxygen partial pressure in said inner space, said pump electrode being composed of a cermet of a noble metal and an oxide having oxygen ion conductivity, wherein said noble metal comprises:
   a first noble metal having a catalytic activity,
   a second noble metal having a catalytic activity suppressing ability to suppress the catalytic activity of said first noble metal with respect to an oxide gas except for oxygen, and
   wherein an abundance ratio of said second noble metal with respect to said first noble metal in a particle surface of said first noble metal existing in said pump electrode is 0.01 to 0.3, wherein said abundance ratio is an area ratio of a part covered with said second noble metal with respect to a part not covered with said second noble metal where particles of said first noble metal itself are exposed in a particle surface of said first noble metal in said pump electrode, and
   wherein said first noble metal is platinum and said second noble metal is gold.

2. The pump electrode of the gas sensor according to claim 1, wherein the abundance ratio of said second noble metal with respect to said first noble metal in the particle surface of said first noble metal existing in said pump electrode is 0.1 to 0.25.

3. A gas sensor to measure a concentration of a gas component in a measurement gas by a limit current method, said gas sensor comprising:
   an inner space;
   an electrochemical pump cell for adjusting an oxygen partial pressure in said inner space, said electrochemical pump cell comprising a pump electrode provided in said inner space, and being composed of a cermet of a noble metal and an oxide having oxygen ion conductivity, wherein said noble metal comprises:
   a first noble metal having a catalytic activity, and
   a second noble metal having a catalytic activity suppressing ability to suppress the catalytic activity of said first noble metal with respect to an oxide gas except for oxygen, and
   wherein an abundance ratio of said second noble metal with respect to said first noble metal in a particle surface of said first noble metal existing in said pump electrode is 0.01 to 0.3, wherein said abundance ratio is an area ratio of a part covered with said second noble metal with respect to a part not covered with said second noble metal where particles of said first noble metal itself are exposed in a particle surface of said first noble metal in said pump electrode, and
   wherein said first noble metal is platinum and said second noble metal is gold.

4. The gas sensor according to claim 3, wherein said pump electrode is formed using a conductive paste manufactured by a method comprising the following steps:
   a) preparing a powder of said first noble metal;
   b) obtaining an ion-containing liquid by dissolving salt or an organic metal complex containing an ion of said second noble metal; and
   c) mixing the powder of said first noble metal, said ion-containing liquid, a powder of said oxide having the oxygen ion conductivity, and a binder.

5. The gas sensor according to claim 3, wherein said pump electrode is formed using a conductive paste manufactured by a method comprising the following steps:
   a) preparing a powder of said first noble metal;
   b) coating the powder of said first noble metal with said second noble metal; and
   c) mixing the coated powder obtained in said step b), a powder of said oxide having the oxygen ion conductivity, and a binder.

* * * * *

UNITED STATES PATENT AND TRADEMARK OFFICE
CERTIFICATE OF CORRECTION

PATENT NO. : 8,366,893 B2
APPLICATION NO. : 12/732298
DATED : February 5, 2013
INVENTOR(S) : Shinji Fujisaki et al.

Page 1 of 1

It is certified that error appears in the above-identified patent and that said Letters Patent is hereby corrected as shown below:

Title Page (30) Foreign Application Priority Data:

Please add "Mar. 26, 2010 (JP) ................. 2010-072533"

Signed and Sealed this
Twenty-eighth Day of May, 2013

Teresa Stanek Rea
*Acting Director of the United States Patent and Trademark Office*